(12) United States Patent
Caillouette

(10) Patent No.: US 6,409,680 B1
(45) Date of Patent: Jun. 25, 2002

(54) PH MEASUREMENT OF BODY FLUID

(76) Inventor: James C. Caillouette, 685 Oak Knoll Cir., Pasadena, CA (US) 91106

(*) Notice: Subject to any disclaimer, the term of this patent is extended or adjusted under 35 U.S.C. 154(b) by 0 days.

(21) Appl. No.: 09/307,478

(22) Filed: May 10, 1999

Related U.S. Application Data

(63) Continuation-in-part of application No. 08/862,032, filed on May 22, 1997, now Pat. No. 5,928,165, which is a continuation-in-part of application No. 08/810,347, filed on Mar. 3, 1997, now Pat. No. 5,738,634, which is a continuation-in-part of application No. 08/376,830, filed on Jan. 23, 1995, now Pat. No. 5,664,579, which is a continuation-in-part of application No. 08/295,399, filed on Aug. 25, 1994, now Pat. No. 5,425,377.

(51) Int. Cl.[7] ............................................. A61B 5/00
(52) U.S. Cl. ..................................................... 600/584
(58) Field of Search ................................. 600/562, 569, 600/572, 573, 584

(56) References Cited

U.S. PATENT DOCUMENTS

| 2,664,879 A | | 1/1954 | Hardy | |
|---|---|---|---|---|
| 2,945,491 A | | 7/1960 | Gibbs | |
| 3,013,656 A | | 12/1961 | Murphy, Jr. | |
| 3,037,496 A | | 6/1962 | Melges | |
| 3,117,569 A | | 1/1964 | Wegner | |
| 3,319,621 A | | 5/1967 | Schwerin | |
| 3,507,269 A | | 4/1970 | Berry | |
| 3,509,872 A | | 5/1970 | Truhan | |
| 3,777,743 A | | 12/1973 | Binard et al. | |
| 4,014,748 A | * | 3/1977 | Spinner et al. | 600/572 |
| 4,018,653 A | * | 4/1977 | Mennen | 600/572 |
| 4,409,182 A | | 10/1983 | Macklem | |
| 4,457,313 A | | 7/1984 | Alter | |
| 4,707,450 A | * | 11/1987 | Nason | 600/572 |
| 4,820,259 A | | 4/1989 | Stevens | |
| 4,862,899 A | | 9/1989 | Bucaro | |
| 5,063,930 A | | 11/1991 | Nucci | |
| 5,078,968 A | * | 1/1992 | Nason | 600/572 |
| 5,147,288 A | | 9/1992 | Schiavo | |
| 5,425,377 A | | 6/1995 | Caillouette | |
| 5,827,200 A | * | 10/1998 | Caillouette | |

FOREIGN PATENT DOCUMENTS

WO    WO-A-97/46878    12/1997

OTHER PUBLICATIONS

Peter Smith, Dept. of Obstetrics & Gynecology, University Hospital, S–751 85 Uppsala, Sweden "Estrogens and the Urogenital Tract".
Gloria Bachmann, Maturitas 22 Suppl. (1995) S21 S29 "The Estradiol Vaginal Ring—A Study of Existing Clinical Data".
"Vulvovaginitis", vol. 1, Chapter 37, Ronald M. Meltzer.
"Urinary Incontinence and Related Urogenital Symptoms in Elderly Women", Ulla Molander, Scandinavian Association of Obstetricians and Gynecologists, Supplement 158, vol. 72, 1993.
"Estrogen Deprivation and Vaginal Function in Postmenopausal Women", James P. Semmens, MD, Gorm Wagner, MD.

* cited by examiner

Primary Examiner—Max Hindenburg
(74) Attorney, Agent, or Firm—William W. Haefliger

(57) ABSTRACT

A support package; a carrier and a detector on the carrier are provided, the carrier removably supported by the package; and a color comparison element or elements are carried by the package to allow color comparison with the detector after its exposure to vaginal or urethral moisture, to detect pH or presence of pathogenic bacteria.

25 Claims, 12 Drawing Sheets

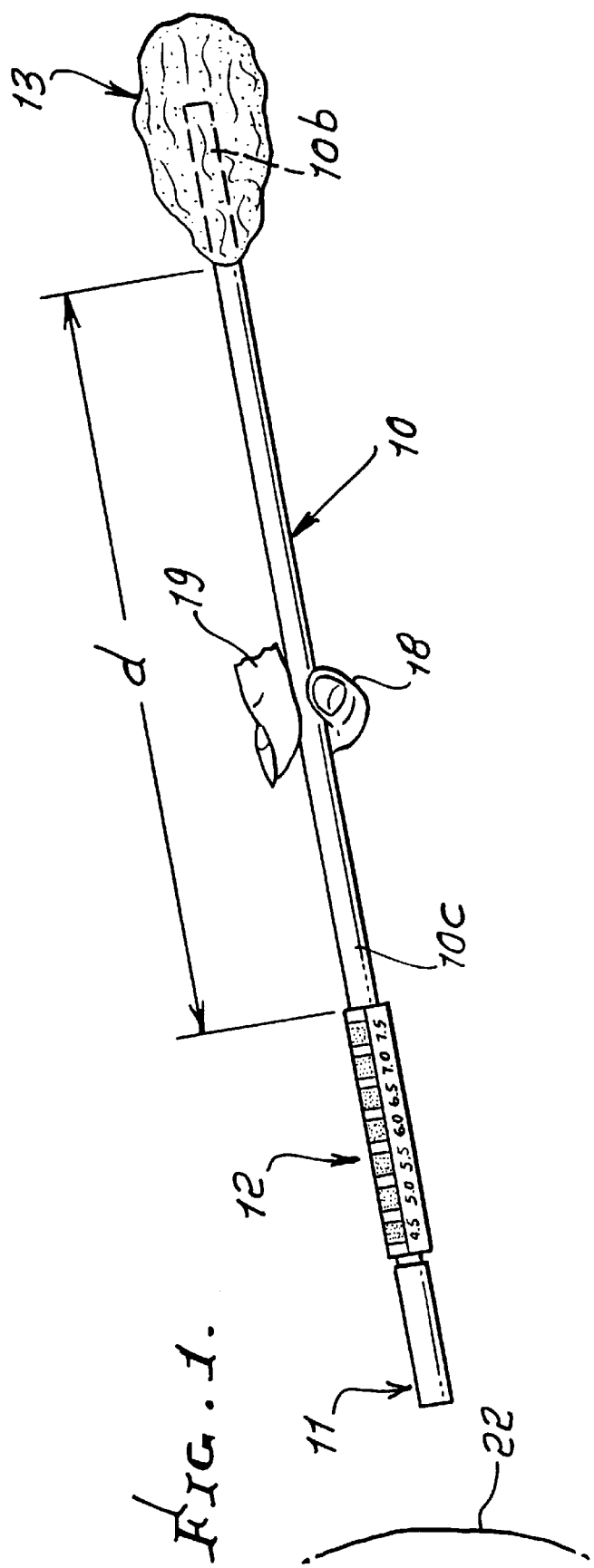
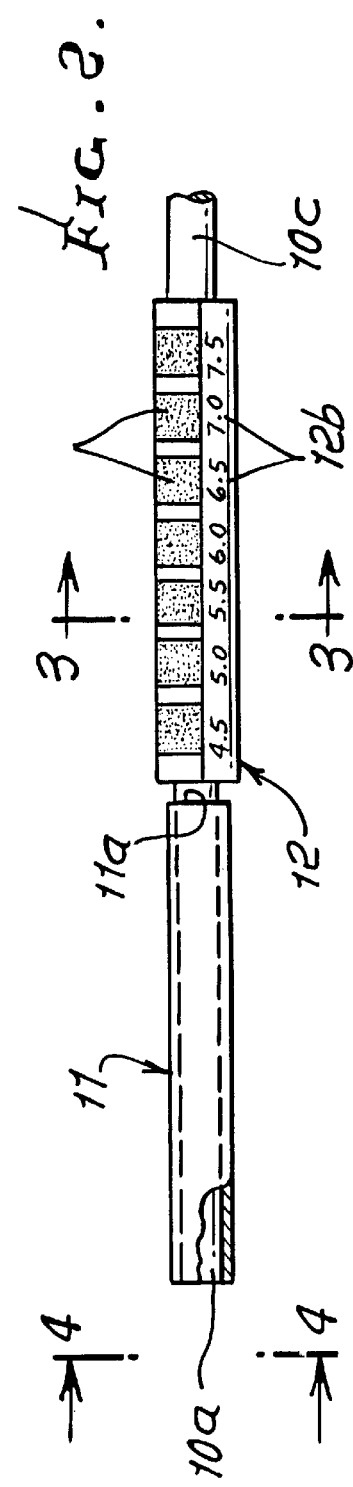

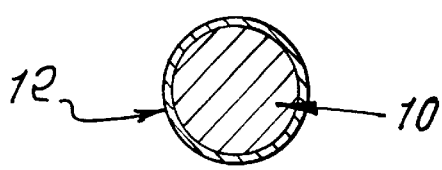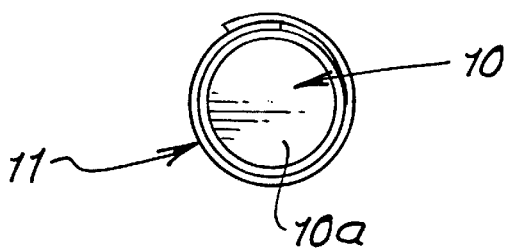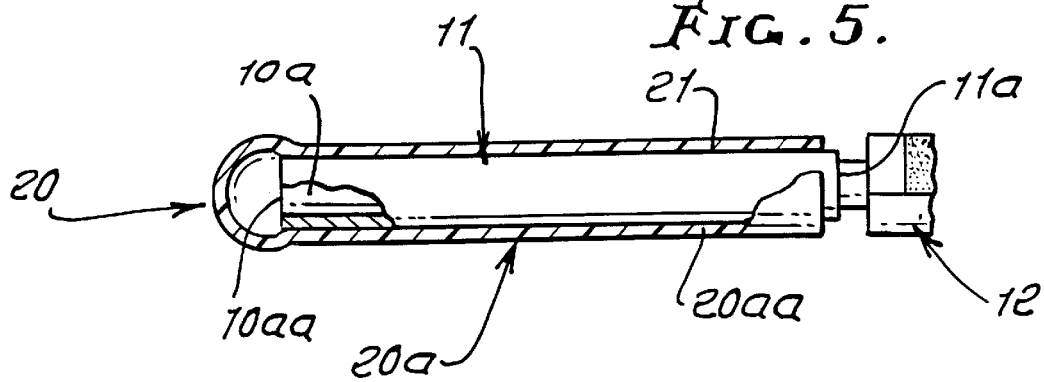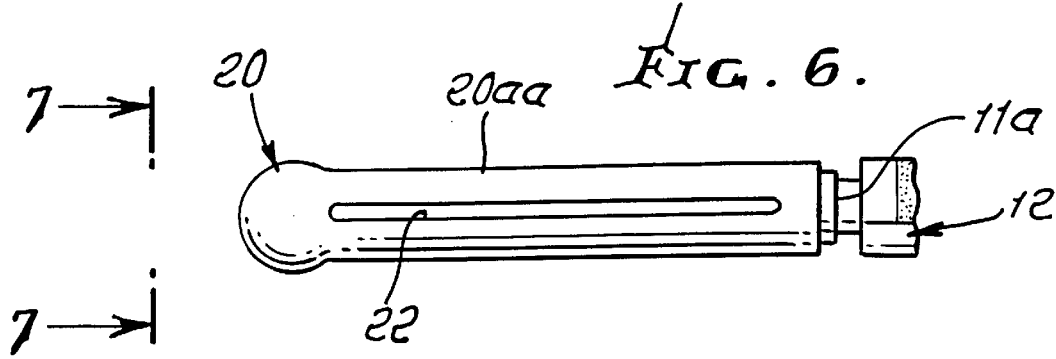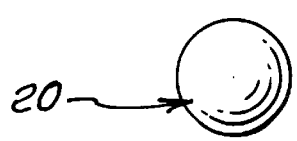

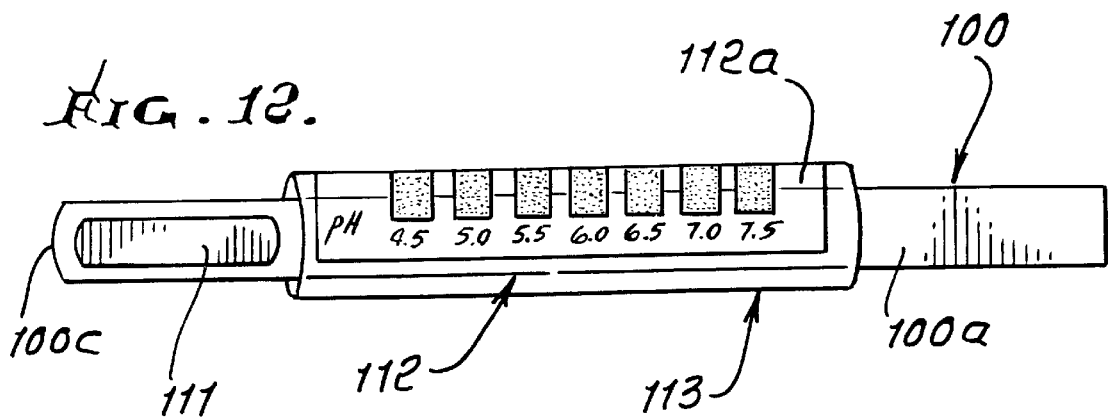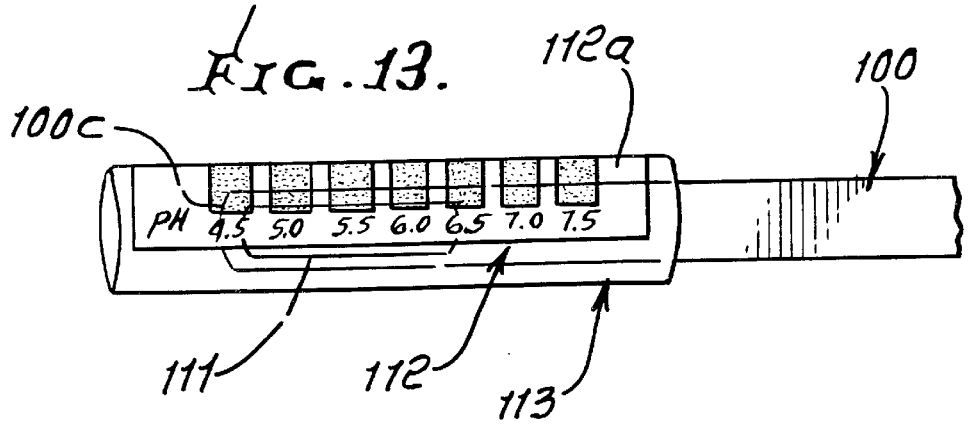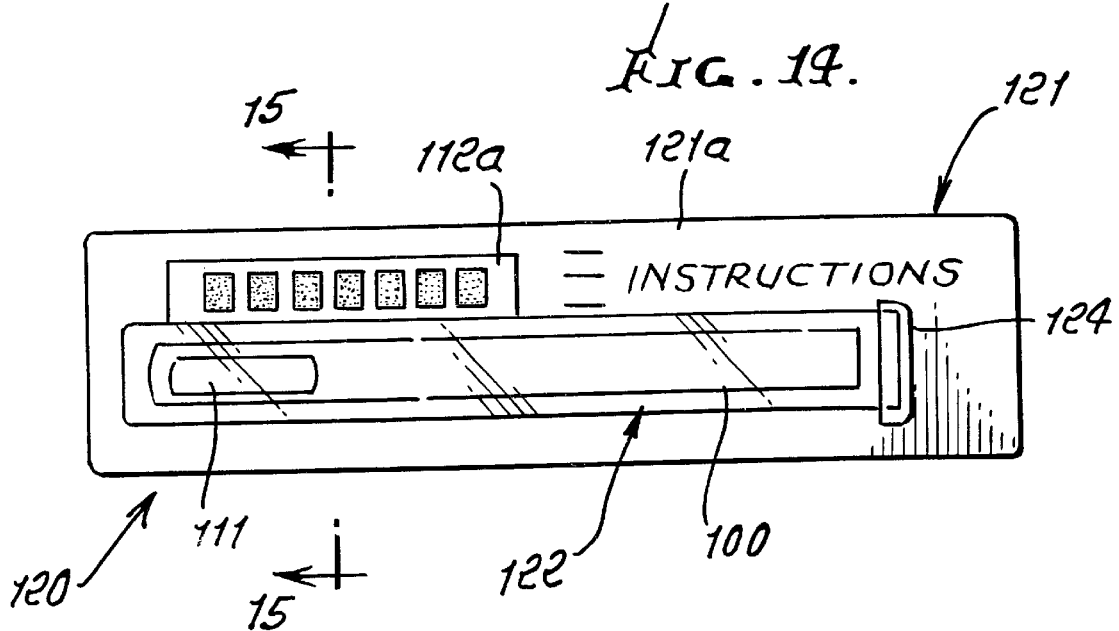

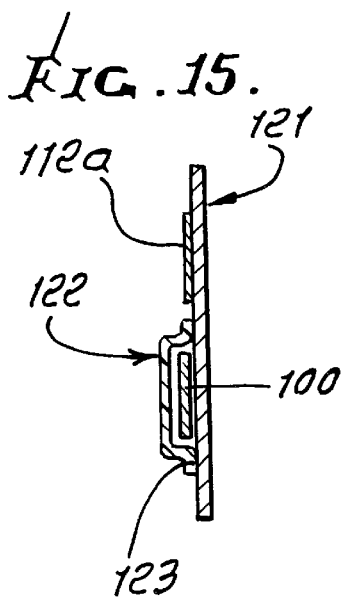
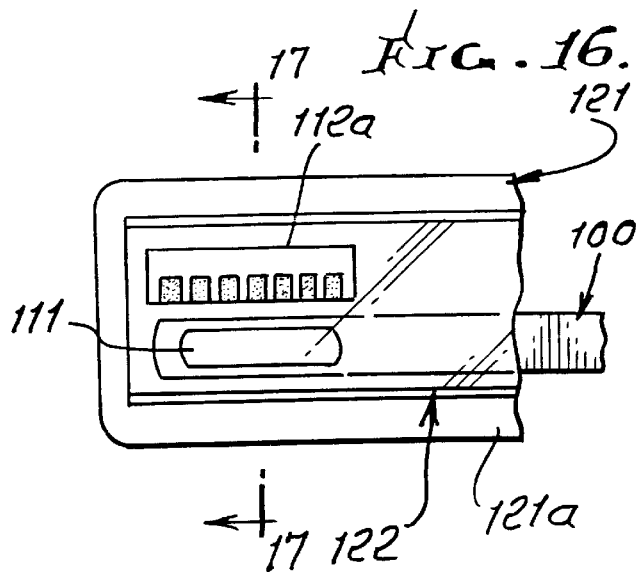
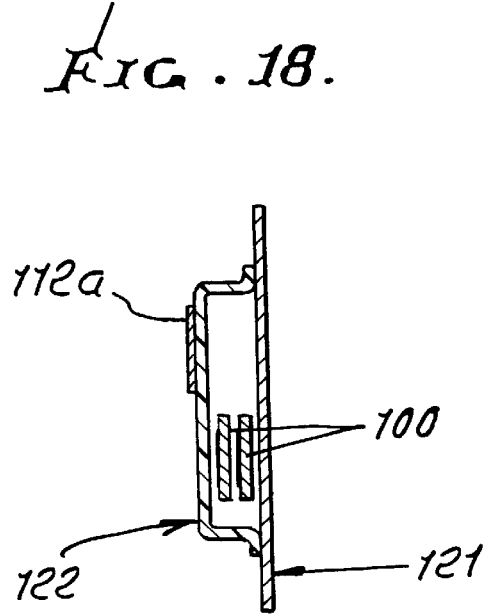
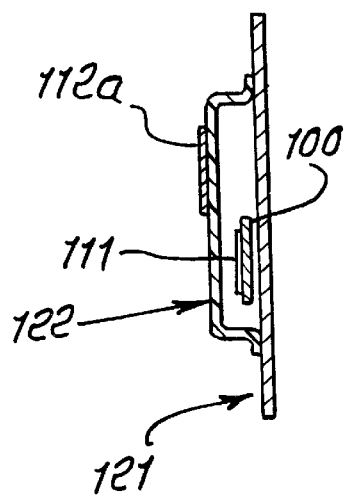

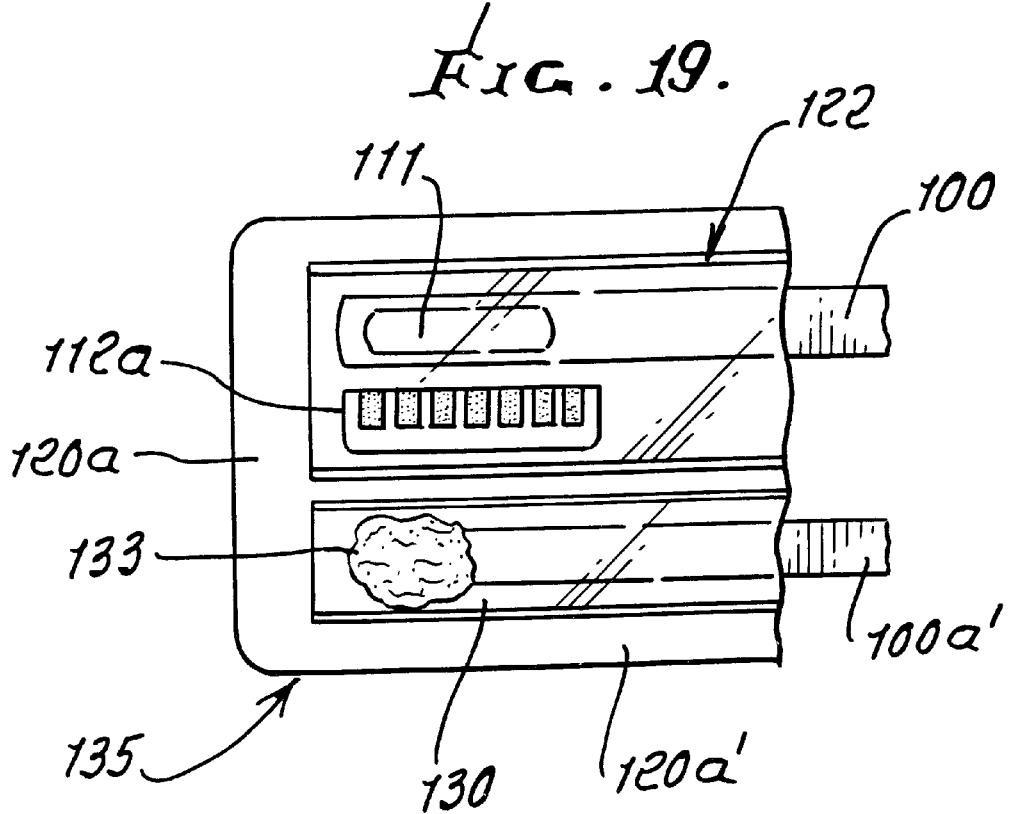
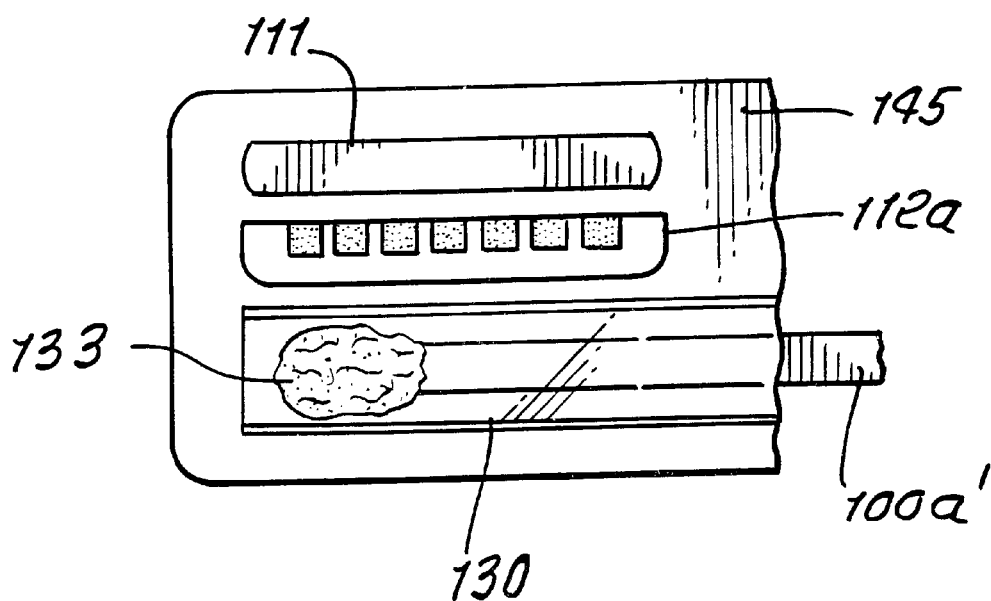

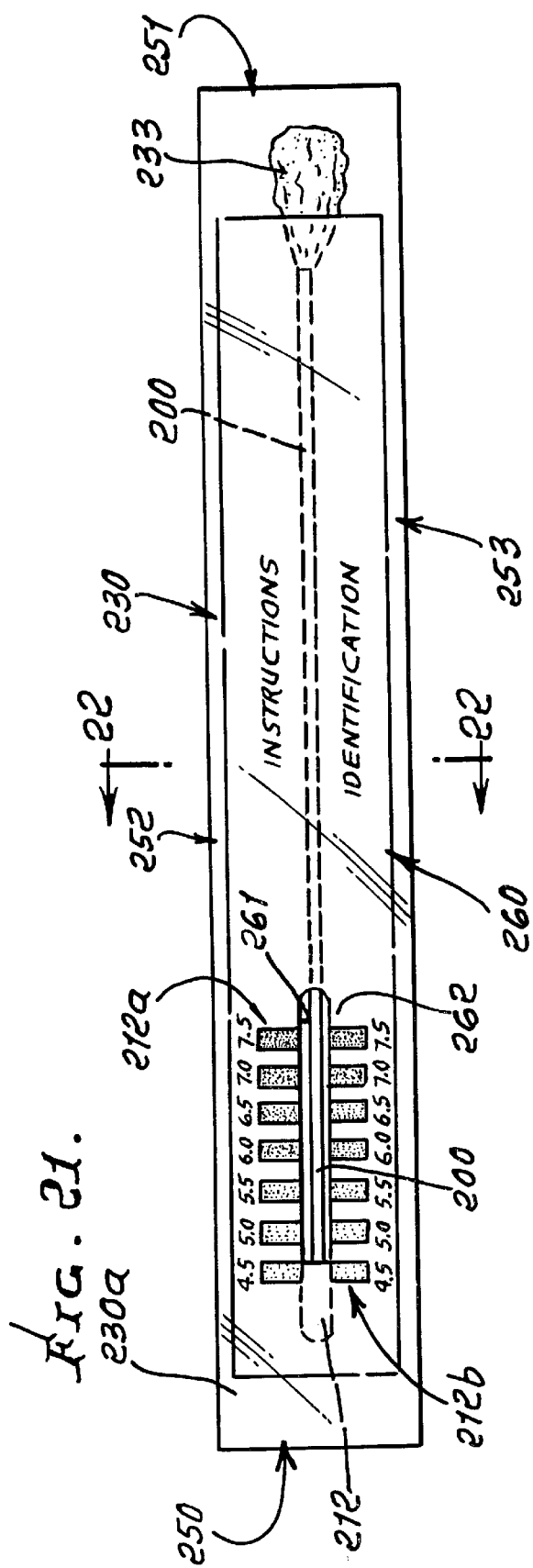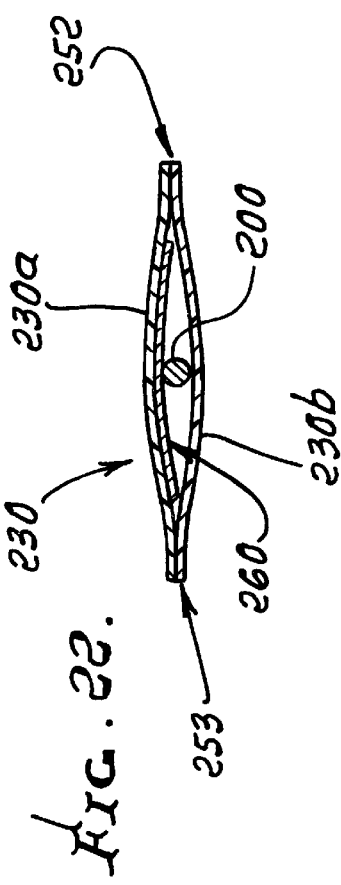

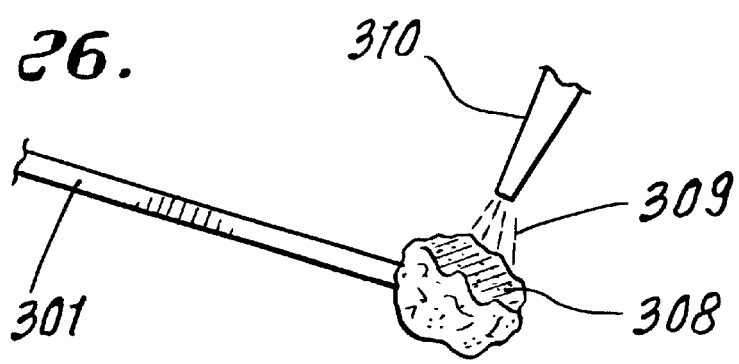
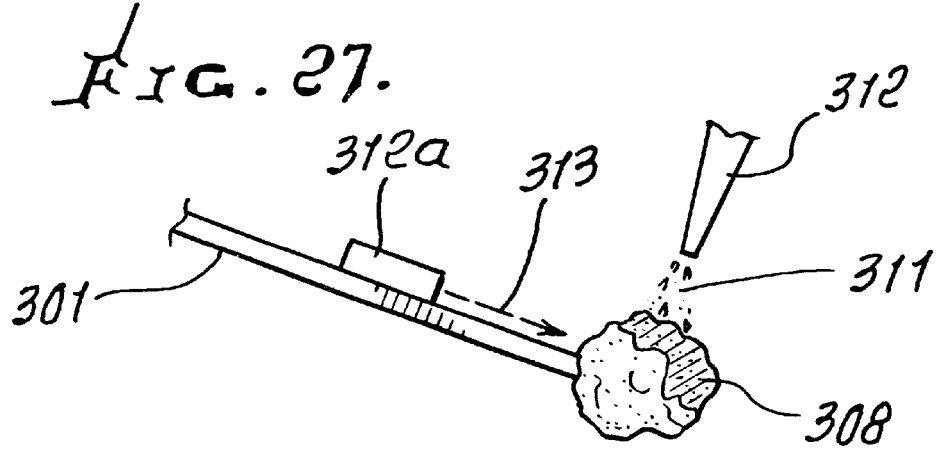
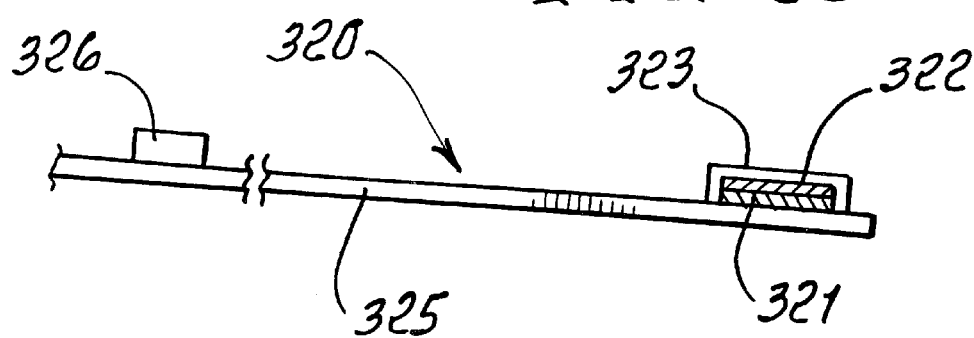

PH MEASUREMENT OF BODY FLUID

This application is a continuation-in-part of prior U.S. patent application Ser. No. 08/862,032, filed May 22, 1997 now U.S. Pat. No. 5,928,165, which is a continuation-in-part of Ser. No. 08/810,347, filed Mar. 3, 1997, now U.S. Pat. No. 5,738,634, which is a continuation-in-part of prior U.S. patent application Ser. No. 08/376,830, filed Jan. 23, 1995, now U.S. Pat. No. 5,664,579, which is a continuation-in-part of prior U.S. patent application Ser. No. 08/295,399, filed Aug. 25, 1994, now U.S. Pat. No. 5,425,377.

BACKGROUND OF THE INVENTION

This invention relates generally to pH measurement of body fluid, such as vaginal and/or urethral fluid, or moisture, and more particularly, to a rapid, easily performed method of obtaining such measurement.

There is continued need to obtain pH measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nitrazine® strip, typically handled by forceps when inserted into the vagina, urethra or other body openings for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination. There is also need to obtain pH measurement of urethral moisture.

There is need for a simple, rapidly carried out method which obviates problems associated with the conventional procedure; also, there is need for ease of excess moisture and mucous removal from the vagina, and/or urethra, at the time of the pH test.

SUMMARY OF THE INVENTION

It is a major object of the invention to provide a significantly improved method which meets the above need, and overcomes prior problems, as referred to. Basically, the method of the invention includes the steps:

a) providing an elongated first carrier, b) providing a pH detector on the carrier at end portion thereof, c) manipulating the carrier to effect exposure of the detector to vaginal or urethral moisture, thereby to cause the detector to exhibit a color change, d) providing a pH correlating color comparison measurement means, in sufficiently close association with the carrier or on the package and with the detector to allow visual comparison of the changed color exhibited by the detector with a pH correlated color provided by the measurement means.

Another object is to provide a package for supporting the first carrier and the color comparison measurement means. In this regard provision may be made for removable containment of the first carrier by the package.

A further object is to provide the detector in the form of an elongated strip, the color comparison measurement means being provided in the form of a strip of material that is elongated in a direction related to the elongated direction of said detector strip to facilitate the color comparison. A method of use typically includes relatively moving the color comparison measurement means and the carrier to achieve the close association of the color comparison measurement means with the detector.

Yet another object includes providing the color comparison measurement strip on the carrier to have thickness that is everywhere less than the thickness of the carrier adjacent the measurement strip. The color comparison measurement strip may be adhered to a package for the pH detector strip on the carrier.

An additional object includes providing the color comparison measurement strip to exhibit a series of colors spaced linearly, and wherein that strip may be located in such relation to said carrier as to position the linearly spaced series of colors in parallel with the elongated detector strip.

A yet further object is to provide the color comparison measurement means on a second carrier that extends at least part way about the first carrier, and to provide the second carrier with a transparent zone to allow visual observation of the detector strip moved into registration with that zone. The second carrier may be provided to have an elongated storage receptacle into which said first carrier, such as a carrier stick, is substantially completely receivable and from which the first carrier is removable to allow its manipulation. That receptacle may provide the transparent zone proximate said color comparison measurement means, to allow ready observation of the detector strip through that zone, for color comparison.

An auxiliary object is to provide a method which includes the steps:

a) providing a pH indication, color comparison measurement, and swabbing means on a carrier stick, b) manipulating the stick between its opposite ends to obtain pH indication of vaginal or urethral moisture at one end of the stick, c) visually interpreting that indication to also obtain pH measurement of such moisture near that one end of the stick, d) again manipulating the stick between its opposite ends, to swab the cervix or urethra, e) and disposing of the stick, whereby disposition of the pH indication, measurement and swabbing means is thereby obtained in one disposal step.

In this regard, the disposal of such a stick may include inserting it into a transparent receptacle, that enables viewing of the pH indication means and color comparison means, protected in the receptacle. A kit may be provided including a support for one such receptacle to receive the carrier stick for the detector, as well as a second receptacle on the support for a second carrier stick, one in which the swab is removably received. The pH indication means on the two sticks may be respectively used to obtain pH indications from vaginal and urethral moisture zones, for comparison check.

As will appear, the a) step may include adhering a pH indication strip to one end of the stick and adhering a pH measurement calorimeter strip to the stick adjacent the pH indication strip, but between the indication strip and the swabbing means, leaving stick extent free for manual manipulation.

A smooth surfaced protective tip may be provided at the strip end of the stick, to facilitate comfortable insertion of that end of the stick in the vagina or urethra, and that tip may be provided in the form of a slotted sleeve fitted over or endwise adjacent the indicator strip. The indicator strip may have a micro-pore cover layer.

It is another object to provide pH measurement means having color gradations in a series sequence, including locating the series lengthwise along the stick, adjacent the indication means. As will be seen, pH measurement means may be provided by winding it about one end of the stick.

A further object includes maintaining an elongated gap along the stick between the pH measurement means and the swabbing means, whereby the stick may be grasped at the gap for manipulation. In this regard, the swabbing means may be provided by attaching a moisture-absorbing swab to the other end of the stick, and in lengthwise spaced relation to both pH indicating means and pH measurement means. The swab may contain an antiseptic or anaesthetic substance.

Yet another object includes the provision of the pH measurement means to have a pH numerical sequence in a series associated with the color gradations, and including also locating the numerical sequence lengthwise along the stick. Apparatus incorporating the invention includes, in combination a) an elongated stick,
b) pH indicating first means on the stick, at one end portion thereof,
c) color comparison pH measurement second means, the stick movable relative to the second means to bring the first means into registration with the second means, for color comparison.

The first means typically comprises a strip adhered to one end of the stick, and the second means may extend lengthwise relative to the stick, and the second means typically has color gradations in a series sequence lengthwise relative to the stick.

An additional object includes the provision of a package for the pH detector strip and stick, and also carrying the color comparison measurement means, as referred to. The package may also provide for packaging of the swab.

Another object is to provide a second detector removably supported by a package. The second detector may be one of the following:

i) a pH detector
ii) an amine detector.

The second detector may be on a swab carried by a stick supported by the package, as in a receptacle.

Yet another object includes provision of a second detector in the form of a reactant characterized as changing color when contacted with moisture containing amine. Such moisture may consist of vaginal or urethral moisture.

A yet further object is to provide improved apparatus, and method, for testing for presence of pathogenic bacteria on or in body moisture, such apparatus including a) a carrier,
b) a moisture receiver on the carrier that may carry an amine produced by the bacteria,
c) said receiver adapted to receive a reactant or reactants to produce a color change if the amine is thereby contacted by the reactant or reactants,
d) and at least one frangible container on the carrier containing said reactant or reactants, whereby the container or containers may be fractured to release said reactant or reactants for contact with moisture in the receiver.

An additional object is to provide two of such frangible containers on the carrier, one containing said one reactant and the other container containing another of the reactants. A support package may support the carrier, such as a stick, and the reactant container or containers on the stick, as will be seen.

These and other objects and advantages of the invention, as well as the details of an illustrative embodiment, will be more fully understood from the following specification and drawings, in which:

DRAWING DESCRIPTION

FIG. 1 is a side elevational view of stick apparatus incorporating the invention:

FIG. 2 is an enlarged side view of one end portion of the FIG. 1 stick apparatus;

FIG. 3 is an enlarged section taken on lines 3—3 of FIG. 2;

FIG. 4 is an enlarged end view taken on lines 4—4 of FIG. 2;

FIG. 5 is an elevation, partly in section, showing a modification;

FIG. 6 is a side elevation of the FIG. 5 modification;

FIG. 7 is an end view taken on lines 7—7 of FIG. 6;

FIG. 12 is a view like FIG. 10, but showing a second carrier extending about the stick of FIG. 10, and relatively slidable lengthwise, the second carrier carrying color comparison measurement elements;

FIG. 13 is a view like FIG. 12 showing the measurement elements registering with the pH detector strip;

FIG. 14 is a plan view of a modification wherein a carrier stick for a pH detector strip is removably contained in a transparent sleeve on a support or substrate, with a color comparison measurement strip also mounted on the support;

FIG. 15 is an enlarged section taken on lines 15—15 of FIG. 14;

FIG. 16 is a view like FIG. 14, but showing a modification;

FIG. 17 is a section taken on lines 17—17 of FIG. 16;

FIG. 18 is a view like FIG. 17, showing a modification;

FIG. 19 is a view like FIG. 16, showing a further modification;

FIG. 20 is a view like FIG. 19 showing a further modification.

FIG. 21 is a view like FIG. 16 showing another modification;

FIG. 22 is a section taken on lines 22—22 of FIG. 21;

FIG. 26 is a view like FIG. 25, showing reactant spray onto the swab;

FIG. 27 is a view like FIG. 26, reactant liquid flowing onto the swab;

FIG. 28 is a view like FIG. 23, but showing a sandwich assembly of components.

DETAILED DESCRIPTION

Figure 8:
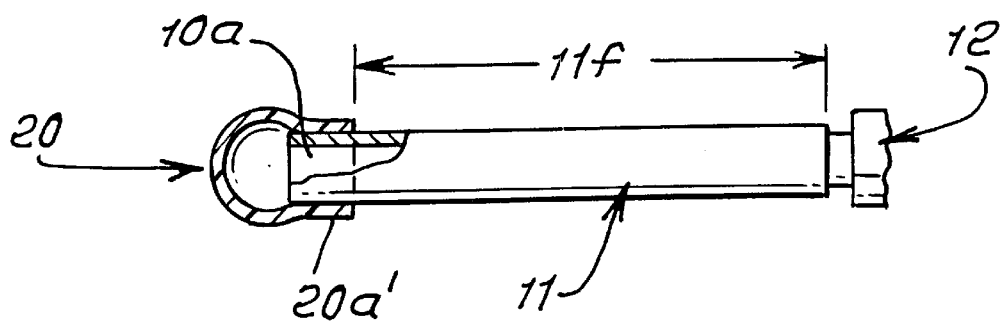
FIG. 8 is an elevation showing a further modification.

In the drawings, an elongated, narrow carrier stick 10 may consist of wood, plastic, or other material. Provided on the carrier stick are:

a pH indication means, as generally shown at 11, at one end portion 10a of the stick;

a color comparison pH measurement means, as generally indicated at 12, spaced from stick end portion 10a, but close to 11; and a swabbing means, as generally indicated at 13 on the opposite end portion 10b of the stick.

As shown, the first means 11 may comprise a pH indication strip, such as a Nitrazine® strip, wound about the stick end portion 10a and adhered to same as by an adhesive. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11;

and immediate visual readout of the pH number adjacent the selected band.

The stick projects freely at 10c away from the first and second means 11 and 12 for manual manipulation (see the grasping finger and thumb 18 and 19), to first obtain pH indication of vaginal or urethral moisture at one end of the stick, and to enable visual interpretation of that indication by color comparison with the second means, without manual release of the stick. The stick is then disposable, or may be disposed of, after a swabbing step to be described.

The swabbing means 13 may comprise a soft cotton swab, or other absorbent material, attached to the carrier stick at its opposite end, and in spaced relation to the first and second means 11 and 12. The lengthwise spacing "d" between 13 and 12 is such as to enable free manual manipulation of the stick; and such spacing is typically between 3 and 5 inches, enabling ready finger grasping of the stick and manipulation thereof, including rapid endwise reversal of the stick. In a specific example "d" is about 4 inches, and the stick diameter is about ⅜ inch.

The method of measuring pH of vaginal or urethral moisture includes the steps:

a) providing a pH indication, color comparison measurement, and swabbing means on a carrier stick, b) manipulating the stick between its opposite ends to obtain pH indication of vaginal or urethral moisture at one end of the stick, c) visually interpreting that indication to also obtain pH measurement of such moisture near that one end of the stick, d) again manipulating the stick between its opposite ends, including endwise reversing it, to swab the vaginal cavity or the urethra in the area from which pH indication was obtained, e) and disposing of the stick, whereby disposition of the pH indication, measurement and swabbing means is thereby obtained in one disposal step.

The overall sizes of 11, 12 and 13 are such as to enable ready insertion into the vagina or urethra, via stick manipulation at zone 10c, with ready stick reversal, as needed. Swabbing of the vagina or urethra indicated at 22 is typically carried out in conjunction with pH measurement, via stick manipulation and endwise reversal, to obtain best measurement results.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina or urethra, for pH measurement. The tip 20 may typically be formed integrally with a sleeve 20a assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal or urethral moisture or fluid may access the strip 11 via that opening. See for example elongated slot 22 in the sleeve wall 20aa. The sleeve and tip may consist of transparent, molded, plastic material, to facilitate viewing of a change of color of the strip 11.

In FIG. 8, the sleeve 20a is shortened and tapered at sleeve end 20a' into flush, or near flush, relation with the surface of the strip, at a locus on stick end portion 10a. This leaves the remaining length 11f of the strip openly exposed for moisture contact.

Figure 9:
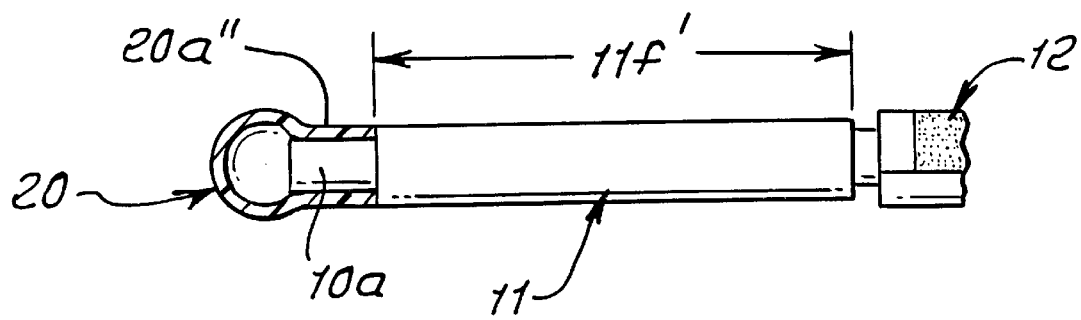
FIG. 9 is an elevation showing yet another modification.

In FIG. 9, the sleeve 20a" is also shortened and attached to the stick end portion 10a, and in endwise alignment with the strip 11. This also leaves the remaining length 11f' of the strip openly exposed for moisture contact.

Figure 10:
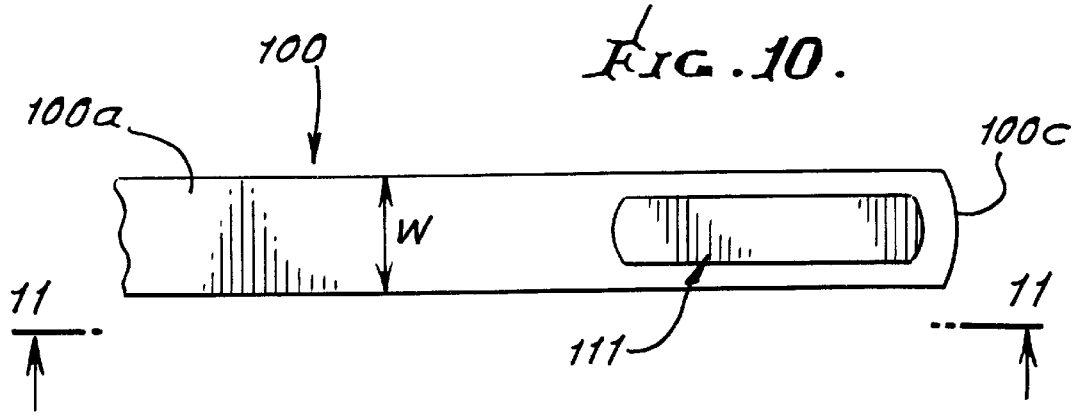
FIG. 10 is a plan view of a modified carrier stick, with a pH detector strip on its surface.
Figure 11:
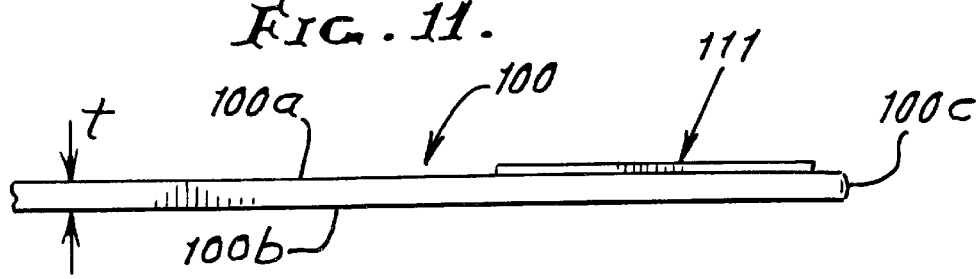
FIG. 11 is an edge view taken on lines 11—11 of FIG. 10.

In FIGS. 10–12, a carrier stick 100 may consist of wood, plastic or other material. It is elongated, and has width "w" and thickness "t", where w exceeds t. The stick has flat opposite sides 100a and 100b, and a smoothly rounded or curved forward end 100c to be inserted into a body cavity, as described above. An elongated pH detector is carried by the stick 100, and may take the form of a Nitrazine® strip 111 adhered to the side 100a of the stick, near convex end 100c, as shown. Typically, strip 111 is thinner than stick thickness "t". Stick 100 enables ease of manipulation to effect exposure of the detector to vaginal or urethral moisture, thereby to cause the detector strip to exhibit color change.

A pH correlating color comparison measurement means is provided in sufficiently close association with said carrier and with said detector to allow visual comparison of the changed color exhibited by said detector with a pH correlated color provided by said measurement means. See for example the second carrier 113 for the color comparison means 112, the carrier 113 being in the form of a sleeve extending at least part way about the stick 100 as seen in FIG. 12. The color comparison means 112 is shown in the form of a series of bands, each having a different color corresponding to a pH level color to which the detector strip may change. See for example the indicated pH levels 4.5, 5.0, 5.5, 6.0, 6.5, 7.0 and 7.5 adjacent the color bands. The bands may be provided on a strip 112a adhered to the sleeve 113. Paper strips providing such elements are known, and sold under the name HYDRION. The band for pH 4.5 is typically bright yellow; the band for pH 6.0 is olive in color; and the band for pH 7.5 is navy blue.

In use, the stick 100 and sleeve 113 are relatively moved, lengthwise, to bring the detector strip 11 (after its exposure to moisture and color change as referred to above) into lateral registration with the color comparison bands, enabling ready visual comparison of the color of the detector strip with the closest color of one of the bands, enabling a pH determination. See FIG. 13. For this purpose, a zone of the carrier sleeve adjacent the bands may be transparent to allow visual observation of the detector, through that zone, adjacent the bands. The entire sleeve and the strip 112a may be transparent.

FIGS. 14 and 15 show a package 120 for the stick 100, detector 111 and color comparison measurement strip 112a that provides the color comparison bands, as referred to. This form of the invention is preferred, although the other forms as described are also desirable and useful.

The package 120 may include a support or substrate 121, such as a cardboard base strip, having a white or other light colored upper surface 121a. A transparent plastic elongated receptacle 122 is mounted on the base, as at 123, and removably receives the stick 100 and detector 111. A cap 124 at the end of the receptacle remote from the detector may be removed to allow stick removal for manipulation as described, to expose the detector to moisture the pH of which is to be determined.

The color comparison measurement strip 112a is adhered to the upper surface of the base. Note that it may be located as shown, proximate the exposed detector 111 as received or re-inserted into the receptacle, after use of the detector. Therefore, a ready, visual, side-by-side comparison of the color of the detector with the color of the bands on strip 112a may be made, and the stick and detector are simultaneously contained, as against contamination, before and after removal for manipulation and use.

FIGS. 16 and 17 show a modified form, which is like FIG. 14, except that color measurement strip 112a is adhered to the transparent plastic, elongated receptacle 122 to be closer to the detector 111 on stick 100 received in the receptacle 122.

FIG. 18 is like FIG. 17, except that the receptacle receives two like sticks 100, each with a detector strip 111 thereon. A redundancy or validity check may be made by use of both sticks to obtain moisture on the detector as from different surface zones of the vagina, or urethra, or from one zone at the vagina, and the other at the urethra, for comparison with the colored bands on color comparison strip 112a.

FIG. 19 shows still another form of the package, the upper portion of which is like that shown in FIG. 17. See identical numerals. The modified package 135 includes a wider base or support 120a, as at 120a', to mount or carry a second transparent plastic receptacle 130. A second stick 100a' has an end swab 133, like swab 13 in FIG. 1 and used for the same purpose. Therefore, a kit is provided to enable pH determination, as well as enable vaginal or urethral swabbing, if desired.

It is contemplated that the swab 133 itself may be treated, or carry, pH detector substance, to change color in accordance with the pH of the moisture it contacts. Therefore, in the FIG. 19 device, the swab 133 acting as a detector, may be compared with the color bands on strip 112a.

FIG. 20 shows a further kit modification, wherein a swab 133 is carried on a stick 100a in a receptacle as at 130, in FIG. 19. The receptacle 122 is not used. Detector strips 111 and color comparison measurement strip 112a are both adhered to the support 145, and in side-by-side relation. In use, the swab 133 is removed from 130 and manipulated on its stick 100a' to become moist due to pick-up of vaginal or urethral moisture. The moist swab 133 is then "swabbed" or rubbed onto detector strip 111, which duly changes color according to pH of the transferred moisture. The color of strip 111 can then be compared to colors on strip 112a.

FIGS. 21 and 22 show yet another kit modification in which an indicator strip or tip 212 (corresponding to strip or tip 111) is carried at the left end of elongated stick 200. A swab 233 is carried at the right end of the stick. An encapsulating, thin, flexible, transparent receptacle 230 protectively contains the elongated stick, tip 212 and swab 233, and may be torn open to retrieve the stick. The receptacle may consist of thin walled plastic sheets 230a and 230b bonded together along sheet edge portions indicated at 250, 251, 252 and 253, whereby the receptacle is sealed.

A thin, elongated paper insert sheet 260 is also received in the receptacle, to overlie most of stick 200, whereby use instruction and identification data may be printed on the sheet 260 and presented upwardly or outwardly for viewing through the transparent upper sheet 230a. Sheet 260 defines a narrow window or cut-out at 261, which is elongated along a mid-portion 262 of sheet 260, as shown.

Color comparison elements such as bands are carried by the insert sheet 260, as in two rows shown at 212a and 212b, at opposite sides of the window. Preferably, the longitudinally spaced bands extend to laterally spaced edges of the window, for ease of color comparison of the indicator (after its exposure to moisture as described above) with the different bands.

Longitudinally spaced bands have different colors, while laterally oppositely spaced bands have the same color. Note their pH numerical labeling, at 4.5, 5.0, 5.5., 6.0, 6.5, 7.0, and 7.5, along the window length.

In use, the right end of the receptacle is opened, and the carrier stick 200 is withdrawn, for use. Thereafter, the indicator tip 212, which may be cylindrical, after its exposure to moisture, is re-inserted into the elongated receptacle 230, under the insert sheet 260, to bring tip 212 under the window 261. Tip 212 preferably has a width or diameter greater than the window width, so that it adjacently registers with the successive bands in the two rows as the tip moves longitudinally. This facilitates ease of color comparison of the tip with the bands. After such color comparison use, the tip and stick remain in the receptacle, for ease of disposal. As an alternative, the insert sheet 260 may be omitted, and the two rows of bands 212a and 212b may be printed directly on the receptacle sheet 230a, which is transparent. Therefore, a window is formed by that portion of sheet 230a between the laterally spaced bands.

The disclosures of applicant's pending applications Ser. No. 08/570,534 filed Dec. 11, 1995, and Ser. No. 08/699,251 filed Aug. 19, 1996 are incorporated herein, by reference.

Figure 23:
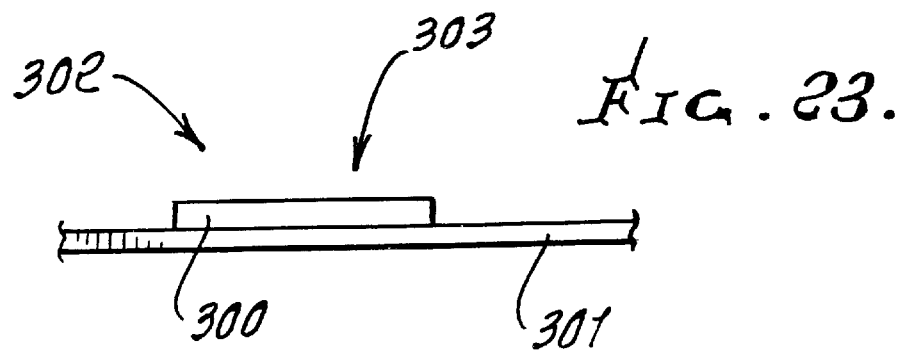
FIG. 23 is a view showing a receiver and received reactant or reactants and moisture.
Figure 24:
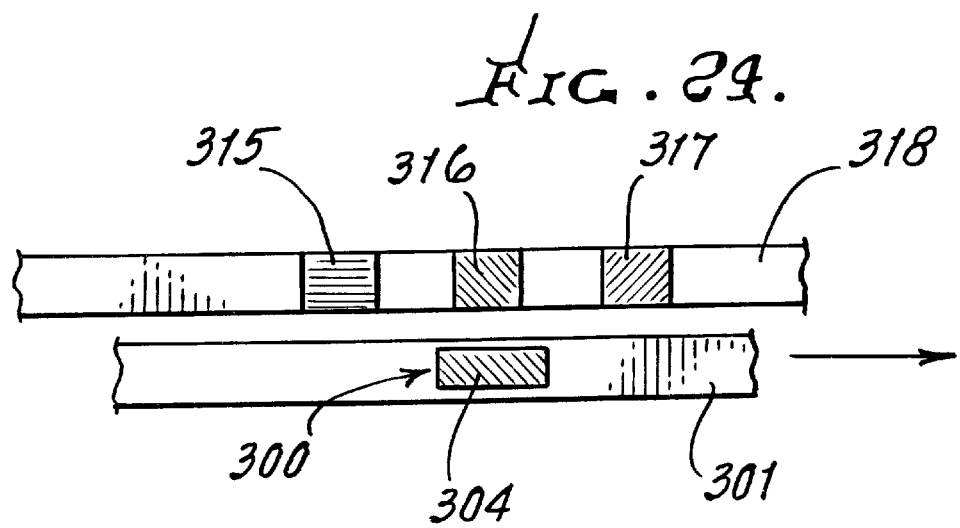
FIG. 24 is a plan view of the FIG. 23 receiver, after color change, and color testing.

FIGS. 23 and 24 illustrate a method of detecting pathogenic bacteria. The steps of the preferred method include a) providing a moisture receiver, onto which moisture containing an amine or amines is receivable, said amine or amines associated with the presence of pathogenic bacteria, b) providing a reactant or reactants which change color, c) and causing said reactant or reactants to contact moisture at the receiver, d) whereby a change in color at the receiver indicates the presence of pathogenic bacteria in said moisture.

As shown, the receiver 300 may advantageously comprise a porous body which may or may not be mounted or carried as at one end of a carrier stick 301. The color changing reactant may be applied to or incorporated on, or in the interstices of the receiver, and may consist, for example, of one or more of the following: Bromocresol Green, Bromocresol Purple, Nitrazine Yellow, Bromophenol Blue, and equivalents. FIG. 23 shows the reactant being applied at 302 to the receiver. Amine carrying moisture is initially applied at 303 to the receiver. When the amine carrying moisture is contacted by color changing reactant and by alkali reactant, a change in color at the receiver indicates the presence of pathogenic bacteria, such color change indicated by surface shading at 304 on receiver 300, in FIG. 24. The alkali reactant may typically consist of liquid (aqueous) potassium hydroxide, powder form sodium aluminate, magnesium hydroxide, sodium carbonate, and sodium hypochlorite, or others as referred to above; and the color change reactant or indicator, changes after addition of the alkali to the amine, or diamine, such as putrecine and/or cadaverine. The reactant or reactants may be distributed as in powder form or on the receiver. The receiver is typically manipulated to control contact of reactant or reactants with moisture received on the receiver, as for example in the vagina to receive vaginal moisture.

Figure 25:
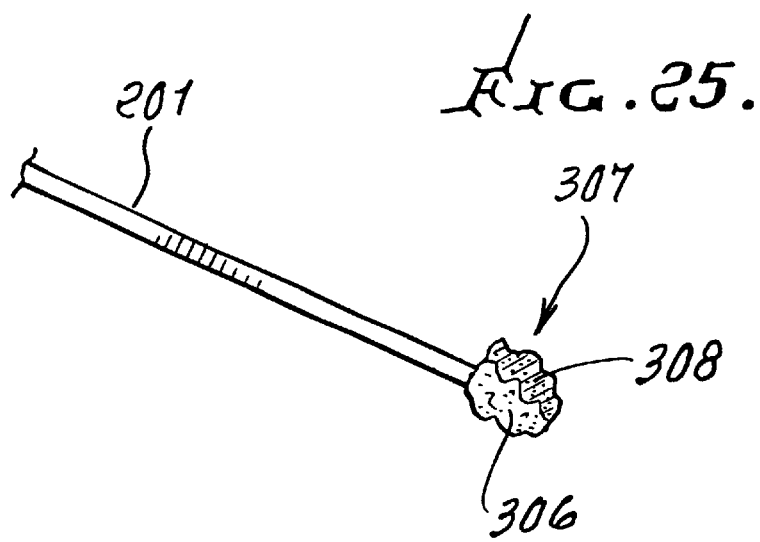
FIG. 25 is a view like FIG. 23, but showing a receiver swab, and color change in response to applied reactant or reactants and moisture.

In a modified form of the method, the reactant is brought into contact with the receiver on which vaginal moisture has been deposited in response to swabbing, the receiver being in the form of a swab. FIG. 25 shows a swab 306 free of reagent during swabbing, but on which vaginal moisture has been deposited. Reagent (first color change reagent and then alkali reagent) is brought into contact with the moisture on the swab, as indicated by the arrow 307. The shaded area 308 indicates a change in color at the receiver or swab, showing presence of pathogenic bacteria. Arrow 307 may represent placement of reactant or reactants onto the swab.

Another example of such contacting is spraying of the reactant in sprayable form onto the swab, as shown at 308 in FIG. 26. The spray 309 discharges from a spraying device 310. A further example of such contacting is flowing of the reactant, in fluid form, indicated by 311 in FIG. 27, onto the swab, to contact vaginal moisture. The fluid reactant or reactants discharge from a fluid container or containers 312, which may for example be free of the carrier stick 301, or which maybe mounted on the carrier stick as at 312*a*. Flow from 312*a* is indicated at 313.

FIG. 24 also shows an optimal confirmation step of obtaining a visual comparison of the color changed zone 304 on the receiver with color, or different colors, or color shades as at 315–317 on a carrier 318. Color 316 may indicate presence of putrecine; color 317 may indicate presence of cadaverine; and color 315 may be another color or color shade close to but different from 316 and 317, and so indicating absence of putrecine or cadaverine, when compared side-by-side with the color on the receiver 300, at 304.

In FIG. 23, the receiver 300 may be a porous body, as for example a bandage, or dressing, or swab, as described above. Body moisture of any type may be applied to the receiver, for testing for presence of pathogenic bacteria. In general, body moisture plus color indicator plus added alkali produce a color change of the indicator when pathogenic bacteria are present in such moisture producing amines such as putrecine and cadaverine. Such a color test obviates need for a so-called "whiff" test sometimes deemed objectionable.

In FIG. 28, a particularly advantageous test apparatus 320 is shown. It includes an elongated carrier 325 which is manually manipulable; a thin layer 321 on the stick and comprising a color indicator; a second thin layer 322 overlying layer 321 and comprising alkali or alkali powder (KOH, or sodium aluminate, or another or others as referred to above, for example); and porous and transparent cover layer 323 overlying 322 and 321. The cover layer may consist of clear, porous, hydrophobic synthetic polymer material, which passes applied moisture to contact layers 321 and 322.

The elongated carrier 325 may carry other test elements, indicated at 326, for testing other human or animal body conditions, or body fluid conditions, such as pH level.

A further aspect of the invention concerns provision of apparatus, which may be provided in a kit including a package, to test for presence of pathogenic bacteria, as in body moisture as for example from the vagina or urethra, or other body cavity. Such apparatus includes a) a carrier, b) a moisture receiver on the carrier that may carry an amine produced by the bacteria, c) the receiver adapted to receive a reactant or reactants to produce a color change if the amine is thereby contacted by the reactant or reactants, d) and at least one frangible container on the carrier containing the reactant or reactants, whereby the container or containers may be fractured to release said reactant or reactants for contact with moisture on or in the receiver.

Figure 29:
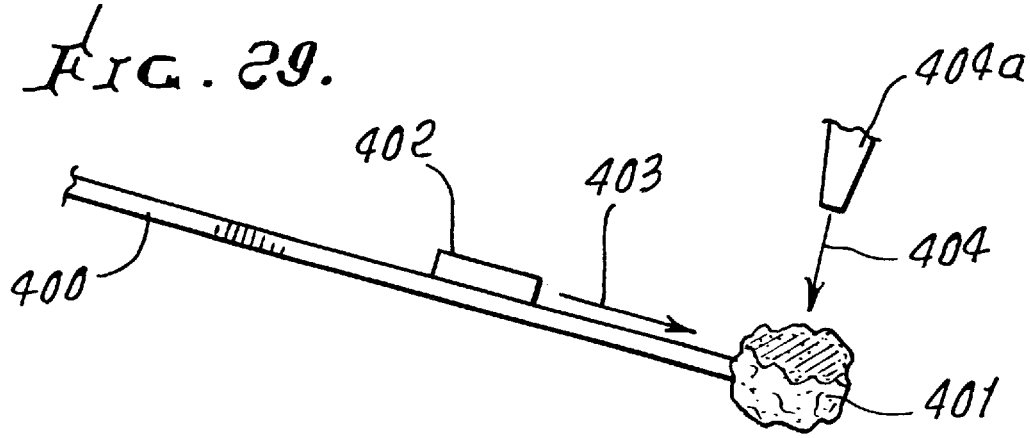
FIGS. 29–34 show further modifications.

Referring to FIG. 29, it shows one such carrier in the form of an elongated stick 400, and a moisture receiver on the carrier, such as a swab 401, for swabbing the body cavity and thereby receiving body moisture which may contain pathogenic bacteria. A single frangible container 402 is carried by the stick, and contains a reactant to be released upon fracture of the container, in order to contact the moisture on the swab. See moisture flow path 403, occurring after fracture of the container. Another reactant may be provided for flow at 404 onto the swab, as from a source 404*a*, and the combination of the two reactants contacting the moisture produces a color change in the event that the moisture contains an amine produced by pathogenic bacteria in the body cavity, as described above. Typical of such amines are cadaverine and putrecine. The first supplied reactant, at 403 or 404 is typically a color change indicator, such as a phenol/dye solution, examples being those described above; and the second supplied reactant (at 404 or 403) is typically an alkali, such as 6% sodium hypochlorite solution (aqueous), or other alkali as described above.

Figure 29A:
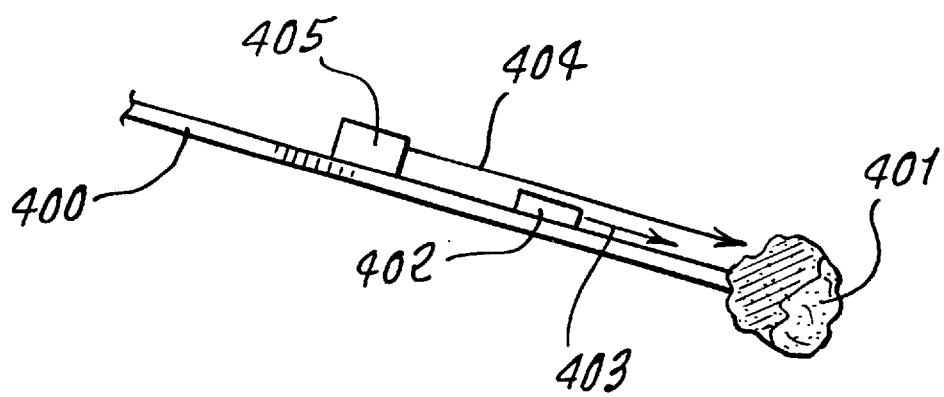
Figure 30:
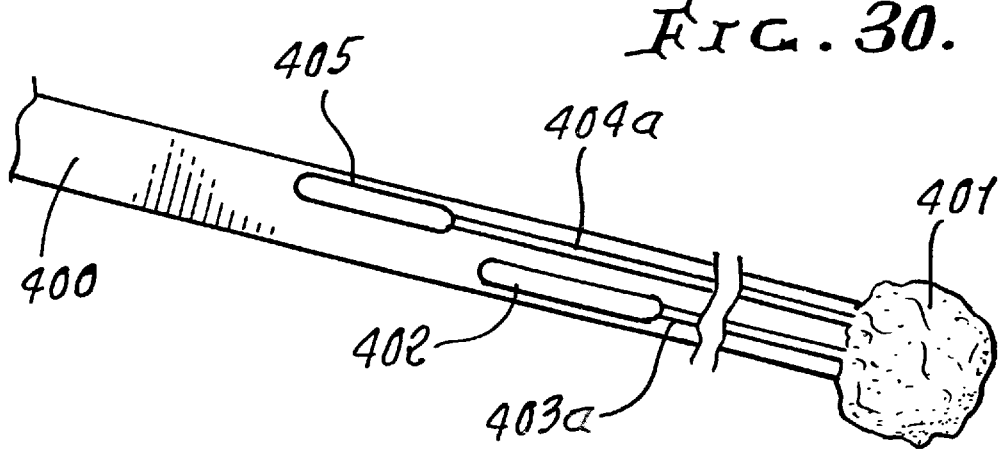

FIG. 29*a* shows two such frangible cartridges 402 and 405 carried by the stick 400, cartridge 402 containing reactant 403, and cartridge 405 containing the reactant 404. Typically, cartridge 402 is fractured (or otherwise actuated) first, for enabling flow of reactant 403 (such as color change indicator) to the swab after its removal from the body cavity, and then cartridge 405 is fractured (or otherwise actuated) for enabling flow of reactant 404 (such as alkali) to the swab, along the indicated flow pathways, typically on or carried by the stick. FIG. 30 is like FIG. 29*a*, but shows such pathways in the form of drain tubes 403*a* and 404*a* extending from the cartridges 402 and 405 to the swab. Such tubes may have sufficient length that the unbroken cartridges are not received in the body cavity, upon use of the swab 401. The stick or carrier may be hollow, to receive and flow reactants to the swab along a common pathway such as a duct.

Figure 31:
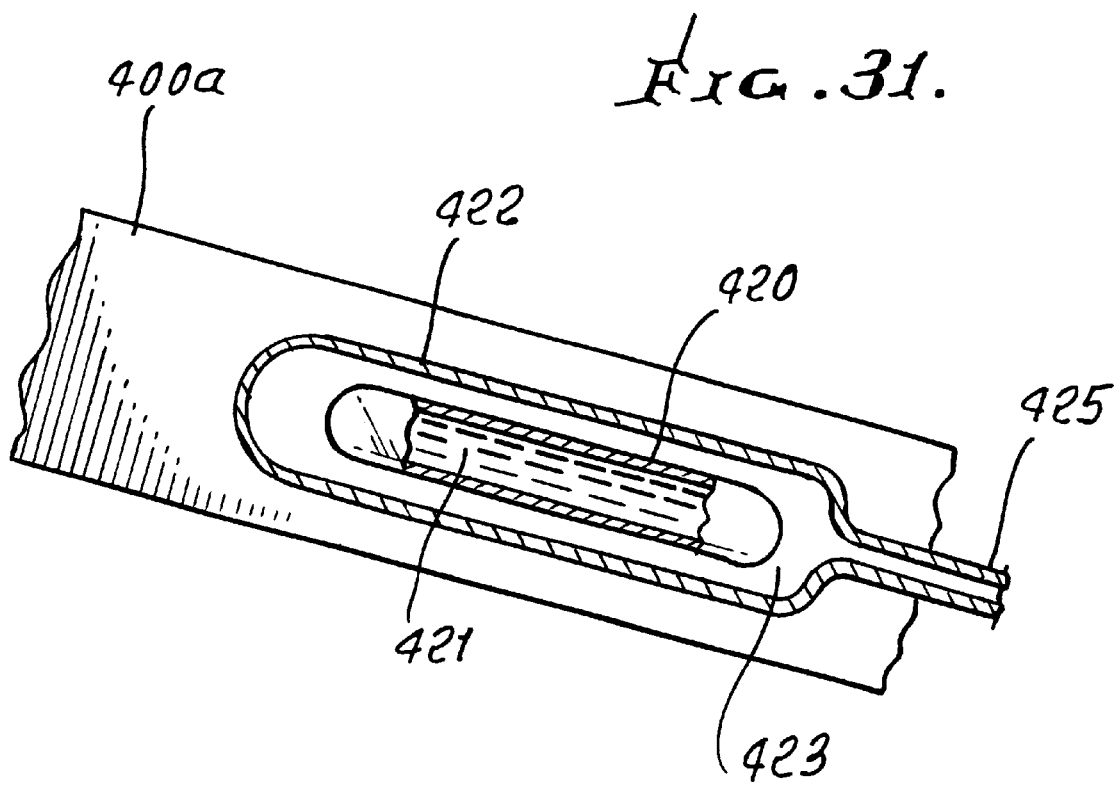

FIG. 31 shows a typical cartridge as including an inner frangible container (glass or plastic) 420 containing reactant 421; and outer shell or capsule 422 housing the container 420. Upon manual fracturing of the container 420, as by bending or deforming capsule 422, the reactant flows into the intermediate space 423, and drains via toward the swab, as via duct 425, in or on the flat stick 400*a*. Reactant 421 may be either of 403 or 404.

Figure 32:
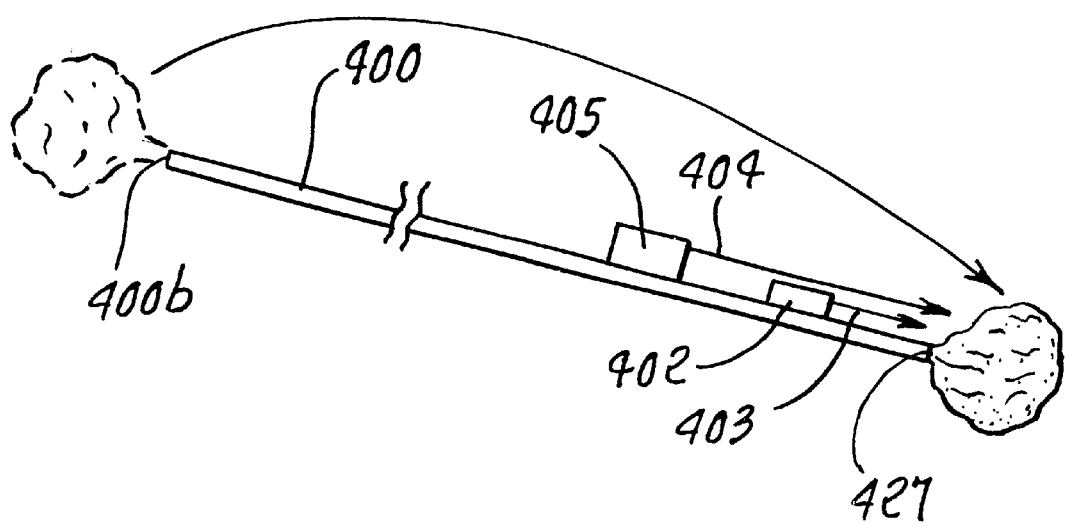

FIG. 32 is like FIG. 29*a*, but the swab 401 has been removed from the remote end 400*b* of the stick 400, where it was used for swabbing, and re-attached at 427 (for example by tongue and groove interfit) to the end of the stick closer to the reactant containers 402 and 405, for reception of reactants flowing at 403 and 404 to contact moisture on the receiver such as swab 401. Line 440 indicates such removal and re-attachment.

Figure 33:
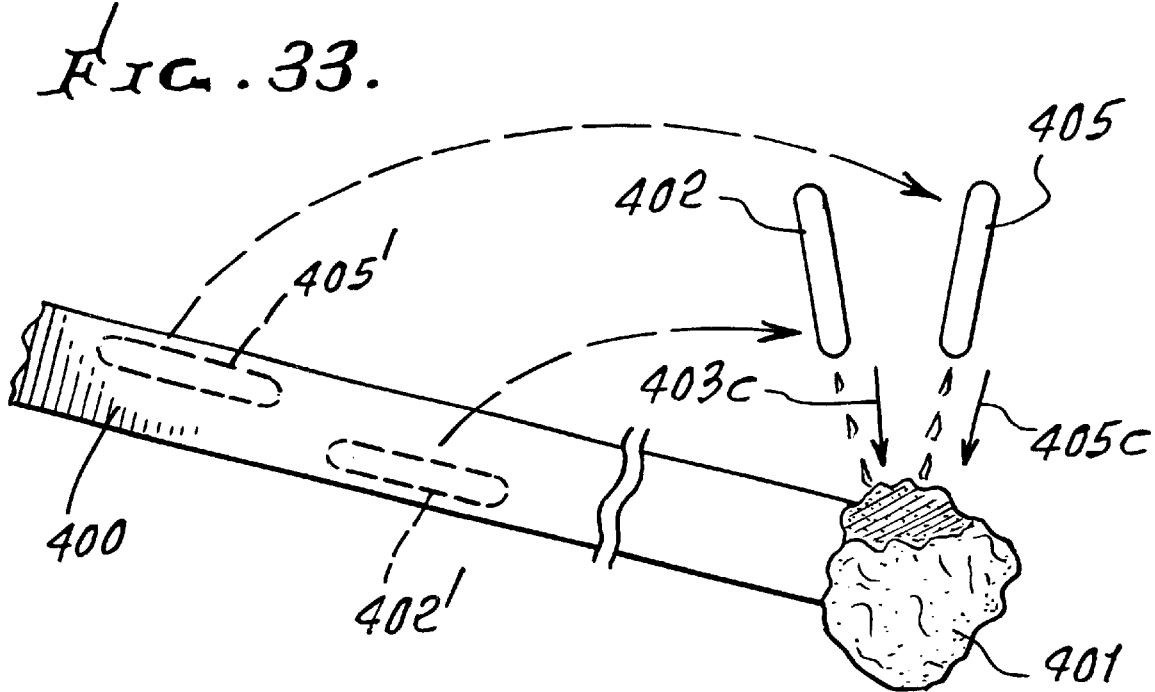

FIG. 33 is like FIG. 29*a*, but the containers 402 and 405 are first manually manipulated to release them from kit stored positions 402' and 405' on the storage stick 400, to be squeezed for fracturing or otherwise actuating the inner cartridges, causing release of reactant to flow at 403c and then at 404c onto moisture on the swab 401. The containers may be releasably retained on the stick by adhesive, enabling their being pulled free of the stick, to be used as described. The stick may thereby be used for swabbing, free of the removed containers, and prior to squeezing of the containers.

Figure 34:
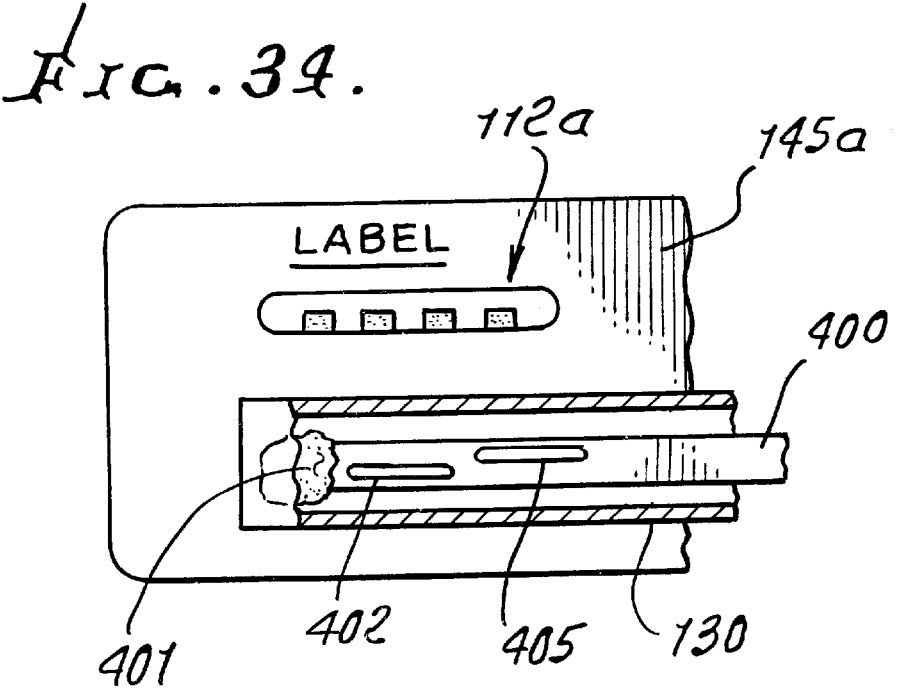

FIG. 34 shows a kit, similar to that of FIG. 20, for storing any of the FIG. 29–33 sticks and containers in a transparent receptacle 130. Color comparison measurement strip 112a is adhered to the support or base 145a, as is the receptacle 130. In use, the stick 400 and swab 401 are removed from 130, and the swab manipulated to pick up moisture, as from a body cavity. After application of reactants, by manipulation of the containers 402 and 405, the changed color of the moist areas of the swab are compared to one or more of the different colors or shades of color 430–435 on the indicator strip 112a, for accurately detecting presence of pathogenic bacteria.

I claim:

1. In apparatus to test for presence of pathogenic bacteria, in body moisture, the combination comprising:
    a) a carrier,
    b) a moisture receiver on the carrier that may carry an amine produced by the bacteria,
    c) said receiver adapted to receive a reactant or reactants to produce a color change if the amine is thereby contacted by the reactant or reactants,
    d) and providing at least one deformable container on the carrier containing said reactant or reactants, whereby the container or containers may be deformed to release said reactant or reactants for contact with moisture in or on the receiver,
    e) and wherein there are two of said deformable containers on the carrier, one containing said one reactant and the other container containing another of the reactants,
    f) and wherein said receiver is carried to receive application of the reactants from the containers.

2. The apparatus of claim 1 wherein reactant contained by one container is selected from the group that includes:
    a) a color change indicator
    b) an alkali.

3. The apparatus of claim 2 wherein said color change indicator is selected from the group that includes: Bromocresol Green, Bromocresol Purple, Nitrazine Yellow, Bromophenol Blue, and equivalents.

4. The apparatus of claim 2 wherein said alkali is selected from the group that includes: potassium hydroxide, powder form sodium aluminate, magnesium hydroxide, sodium carbonate, and sodium hypochlorite.

5. The apparatus of claim 1 including a support package supporting said carrier.

6. The apparatus of claim 5 wherein the package includes receptacle means for the carrier.

7. The apparatus of claim 1 wherein one reactant is a color change indicator, and the other reactant is an alkali.

8. The combination of claim 1 wherein said receiver is located at an end portion of the carrier, and said containers are spaced from the receiver.

9. The combination of claim 8 including a pathway or pathways on the carrier to conduct said reactants along the carrier toward the receiver.

10. The combination of claim 9 wherein said pathway or pathways comprise a duct or ducts.

11. The combination of claim 5 including a color comparison element or elements carried by the apparatus.

12. In apparatus to test for presence of pathogenic bacteria, in body moisture, the combination comprising:
    a) a carrier,
    b) a moisture receiver on the carrier that may carry an amine produced by the bacteria,
    c) said receiver adapted to receive a reactant or reactants to produce a color change if the amine is thereby contacted by the reactant or reactants,
    d) and providing at least one deformable container on the carrier containing said reactant or reactants, whereby the container or containers may be deformed to release said reactant or reactants for contact with moisture in or on the receiver,
    e) and wherein there are two of said frangible containers on the carrier, one containing said one reactant and the other container containing another of the reactants,
    f) and wherein said receiver is carried for movement to a position spaced from an end portion of the carrier, to receive application of the reactants from the containers.

13. In the method to test for presence of pathogenic bacteria, in body moisture, the steps that include:
    a) providing a carrier,
    b) providing a moisture receiver on the carrier that may carry an amine produced by the bacteria,
    c) said receiver adapted to receive a reactant or reactants to produce a color change if the amine is thereby contacted by the reactant or reactants,
    d) and providing at least one deformable container on the carrier containing said reactant or reactants, whereby the container or containers may be deformed to release said reactant or reactants for contact with moisture in or on the receiver,
    e) and including receiving said bacteria produced amine onto the receiver, and said reactant or reactants, when released, onto the receiver.

14. The method of claim 13 wherein reactant contained by the container is selected from the group that includes:
    a) a color change indicator
    b) an alkali.

15. The method of claim 14 wherein said color change indicator is selected from the group that includes: Bromocresol Green, Bromocresol Purple, Nitrazine Yellow, Bromophenol Blue, and equivalents.

16. The method of claim 14 wherein said alkali is selected from the group that includes: potassium hydroxide, powder form sodium aluminate, magnesium hydroxide, sodium carbonate, and sodium hypochlorite.

17. The method of claim 13 including providing a support package supporting said carrier.

18. The method of claim 17 including providing receptacle means for the carrier, and associated with the package.

19. The method of claim 13 wherein two of said frangible containers are provided on the carrier, one containing said one reactant and the other container containing another of the reactants.

20. The method of claim 19 wherein one reactant is a color change indicator, and the other reactant is an alkali.

21. The method of claim 19 wherein said receiver is provided at an end portion of the carrier, and said containers provided are to be spaced from the receiver.

22. The method of claim 21 including providing a pathway or pathways on the carrier to conduct said reactants along the carrier toward the receiver.

23. The method of claim 22 wherein said pathway or pathways are provided in the form of a duct or ducts.

24. In the method to test for presence of pathogenic bacteria, in body moisture, the steps that include:
  a) providing a carrier,
  b) providing a moisture receiver on the carrier that may carry an amine produced by the bacteria,
  c) said receiver adapted to receive a reactant or reactants to produce a color change if the amine is thereby contacted by the reactant or reactants,
  d) and providing at least one deformable container on the carrier containing said reactant or reactants, whereby the container or containers may be deformed to release said reactant or reactants for contact with moisture in or on the receiver,
  e) and wherein two of said frangible containers are provided on the carrier, one containing said one reactant and the other container containing another of the reactants,
  f) and including moving the receiver to a position spaced from an end portion of the carrier, to receive application of the reactants from the containers.

25. The method of claim 17 including providing a color comparison element or elements carried by the package.

* * * * *